US00PP15680P3

(12) United States Plant Patent
Williams

(10) Patent No.: US PP15,680 P3
(45) Date of Patent: Mar. 22, 2005

(54) HYBRID TEA ROSE PLANT NAME 'JASPER CRANE'

(50) Latin Name: *Rose hybrid*
Varietal Denomination: Jasper Crane

(76) Inventor: J. Benjamin Williams, 2800 Elnora St., Silver Spring, MD (US) 20901

( * ) Notice: Subject to any disclaimer, the term of this patent is extended or adjusted under 35 U.S.C. 154(b) by 29 days.

(21) Appl. No.: 10/056,432

(22) Filed: Jan. 24, 2002

(65) Prior Publication Data

US 2003/0140386 P1 Jul. 24, 2003

(51) Int. Cl.[7] ..... A01H 5/00
(52) U.S. Cl. ..... Plt./140
(58) Field of Search ..... Plt./139, 140

*Primary Examiner*—Howard J. Locker
(74) *Attorney, Agent, or Firm*—RatnerPrestia

(57) ABSTRACT

A new and distinct variety of rose plant of the hybrid tea class, characterized by its continuous production of brilliant red well-formed blooms on long straight stems, its vigorous upright habit of growth, its excellent branching, its large open flowers and its intense rose fragrance.

1 Drawing Sheet

FIELD OF THE INVENTION

This invention relates to a new and distinct variety of rose plant of the hybrid tea rose class.

SUMMARY OF THE INVENTION

The invention is a new and distinct variety of rose plant of the hybrid tea class, which was originated by me by crossing the rose variety known as 'Mister Lincoln' (U.S. Plant Pat. No. 2,370) with the variety known as 'Chrysler Imperial' (U.S. Plant Pat. No. 1,167). As a result of this breeding, I have produced a new and improved rose variety which is distinguished from its parents, as well as from all other rose varieties of which I am aware, as evidenced by the following unique combination of characteristics which are outstanding therein:

(1) Continuous production of brilliant red well-formed blooms on long straight stems.
(2) Vigorous upright habit of growth.
(3) Excellent branching.
(4) Large open flowers.
(5) Intense rose fragrance.

Asexual reproduction of this new variety by budding was first performed in West Grove, Chester County, Pa., U.S.A. Asexual reproduction of this new variety in West Grove, Pa., U.S.A., shows that the foregoing and all other characteristics come true to form and are established and transmitted through successful propagation.

BRIEF DESCRIPTION OF THE ILLUSTRATION

The accompanying illustration shows typical specimens of the vegetative growth and flower of this new variety, depicted in color as nearly true as it is reasonably possible to make the same in a color illustration of this character.

DETAILED DESCRIPTION OF THE NEW VARIETY

The following is a detailed description of my new rose cultivar with color descriptions using terminology in accordance with a Royal Horticulture Society Colour Charts (R.H.S.C.C.), except where ordinary dictionary significance of color is indicated.

Parentage: Seedling.
*Seed parent.*—'Mister Lincoln' (U.S. Plant Pat. No. 2,370).
*Pollen parent.*—'Chrysler Imperial' (U.S. Plant Pat. No. 1,167).
Class: Hybrid tea.

The following observations are made of three-year old specimens grown outdoors in Kent County, Md., and New Castle County, Del., during the months of June and October.

FLOWER

Blooming habit: Recurring, continuous.

A. Bud:
*Size.*—Large. About 2 to 2½ inches long when the petals start to unfurl.
*Form.*—Long and pointed.
*Color.*—Red Group 53B when sepals start to unfurl.
*Sepals.*—Medium, tapered, curling back as bud opens extending ⅓–½ the length of the open bud. Length: about 1¼ to 1¾ inches. There are three normally appendaged sepals. There are two unappendaged sepals with hairy edges. Shape: triangular, pointed with slight serration at tip. Texture: smooth. Color: Upper side: Yellow Green Group 144A; Underside: Green Group 138C.
*Peduncle.*—Length: 3½ to 5 inches. Strength: straight, erect, and heavy. Aspect: slightly hairy. Color: Yellow Green Group 144A.
*Calyx tube.*—Length: about ¼ to ½ inch. Aspect: smooth. Color: Yellow Green Group 144C.

B. Bloom:
*Size.*—Large. Average open size is 5 to 5½ inches.
*Borne.*—Singly.
*Stems.*—Very long. Average length about 1½ to 3 feet.
*Form.*—When first open: High centered. With outer petals recurling backwards and retains its form to the end.

*Petalage.*—Length typically about 1½ to 3 inches. Width typically about 1¾ to 2¼ inches. Number of petals under normal conditions: about 38.

*Color.*—Dark red — When first opened, the upper side is Red Group 53B. The underside is Red Group 53B.

*Color change.*—As the bloom ages, the edge of the upper side of the petals tend to Red Purple Group 79A. The underside tends to Red Purple Group 71A.

*Fragrance.*—Strong rose fragrance.

C. Petals:

*Texture.*—Velvety.

*Shape.*—Cup shaped with a rounded point neat the center of the outermost margin.

*Margins.*—Entire.

*Petal attachment.*—Yellow Green Group 154C.

*Arrangement.*—Symmetrically arranged in a circular outline.

*Persistence.*—Drop off cleanly.

*Lasting quality.*—On the plant: Long, 7–10 days. As a cut flower: 9–12 days.

REPRODUCTIVE PARTS

A. Reproductive parts:

*Stamens.*—Length: about ¼ to ½ inch. Color: Greyed Orange Group 163A.

*Anthers.*—Size: Medium, about ⅛ inch. Quantity: Many, about 100. Color: near Greyed Orange Group 164A. Arrangement: Regular around styles.

*Filaments.*—Color: near Red Group 39A.

*Pollen.*—Color: Greyed Orange Group 164C.

*Styles.*—Color: Greyed Orange Group 164D.

*Stigmas.*—Color: Greyed Orange Group 164D.

*Pistils.*—Many, about 80 to 100; Length — about ½ inch.

B. Hips: Few.

C. Seeds: Not observed.

PLANT

A. Form: Upright.

B. Growth: Very vigorous, uniform branching on main stems, new growth occurs regularly throughout the season. Height obtained in first season — 4 to 6 ft. Mature Plant: Tall. Height — 4 to 6 ft. Width — 2½ to 3½ ft.

C. Foliage:

*Leaves.*—Compound: 3 to 5 leaflets on single bloom, 5 to 7 leaflets on main canes.

*Size.*—Medium. Leaflets — 1½ to 3¾ inches long and ½ to 2 inches wide.

*Quantity.*—Abundant, covers plant to ground.

*Arrangement.*—Alternate; uniform and equally spaced.

*Leaf bud.*—Red Group 46A.

*Color.*—New foliage: Upper side — Edge: Greyed Purple Group 183A. Center: Yellow Green Group 146B. Under side — Edge: Greyed Purple 183D. Center: Yellow Green Group 146C. Old foliage: Upper side: Yellow Green Group 146A, Under side: Yellow Green Group 147B.

*Shape.*—Oval with slight point at tip.

*Venation.*—Parallel.

*Texture.*—Upper side — leathery, smooth. Under side — smooth between ribs.

*Edge.*—Serrated.

*Serration.*—Very small and uniform.

*Petiole.*—Color: Upper side — Yellow Green Group 146B. Under side — Yellow Green Group 146B. Texture — Smooth. Length — 2½ to 4 inches.

*Rachis.*—Color — Yellow Green Group 146A. Texture — Smooth.

*Stipules.*—Shape — Pointed. Texture — Medium smooth. Color — Yellow-Green Group 146C. Length — ½ to 1 inch.

*Resistance to disease.*—Blackspot — resistant. Mildew — resistant. Rust — not observed.

D. Wood:

*New wood.*—Color — Greyed Purple Group 183C. Bark — smooth.

*Old wood.*—Color — Yellow-Green Group 146A. Bark — smooth.

E. Thorns and prickles:

*Thorns.*—Quantity — ordinary. On laterals — ordinary. Shape — pointed and curved down. Length — about ¼ inch. Color (when young) — Greyed Orange Group 177C, (when mature) — Greyed Orange Group 164C. Position — irregular.

*Prickles.*—Quantity — very few. On laterals — very few. Size — about ⅛ inch. Shape — pointed. Position — irregular.

F. Winter hardiness: Excellent. Hardy to zone 4.

I claim:

1. A new and distinct variety of rose plant of the hybrid tea class, substantially as herein shown and described, characterized particularly as to novelty by its continuous production of brilliant red well-formed blooms on long straight stems, its viorous upright habit of growth, its excellent branching, its large open flowers, and its intense rose fragrance.

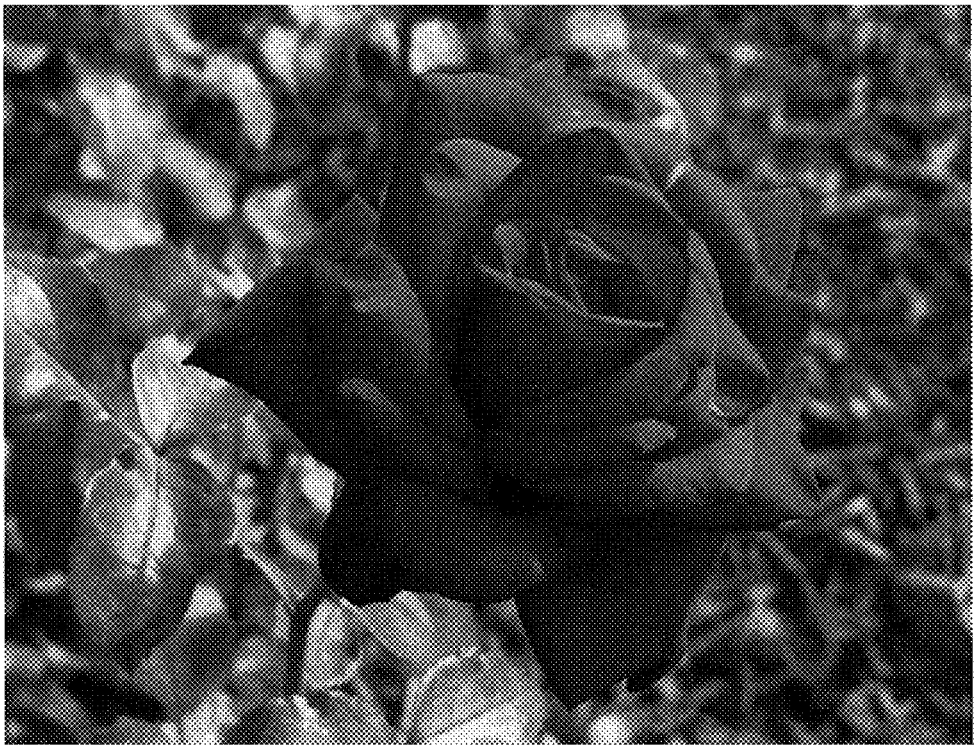

* * * * *